United States Patent [19]
Girard et al.

[11] Patent Number: 5,937,886
[45] Date of Patent: Aug. 17, 1999

[54] METHOD AND DEVICE FOR DELIVERING A PURE GAS CHARGED WITH A PREDETERMINED QUANTITY OF AT LEAST ONE GASEOUS IMPURITY TO AN APPARATUS

[75] Inventors: Jean-Marc Girard, Paris; Alain Mail, Domene; Yves Marot, Buc, all of France

[73] Assignee: L'Air Liquide, Societe Anonyme pour l'Etude et l'Exploitation des Procedes Georges Claude, France

[21] Appl. No.: 08/752,070

[22] Filed: Nov. 19, 1996

[30] Foreign Application Priority Data

Nov. 5, 1996 [FR] France ................................. 96 13436

[51] Int. Cl.$^6$ ........................................................ F17D 1/04
[52] U.S. Cl. ........................... 137/3; 137/605; 137/606; 137/872; 137/863; 137/599.1; 137/599; 251/331; 73/1.06
[58] Field of Search ............................... 137/2, 7, 3, 597, 137/599, 599.1, 602, 605, 606, 863, 872; 73/1.02, 1.06; 251/331

[56] References Cited

U.S. PATENT DOCUMENTS

| | | | |
|---|---|---|---|
| 4,977,929 | 12/1990 | Chinnock | 137/863 |
| 5,157,957 | 10/1992 | Mettes | 137/7 |
| 5,239,856 | 8/1993 | Mettes | 73/1.06 |
| 5,261,452 | 11/1993 | McAndrew | 73/1.06 |
| 5,497,652 | 3/1996 | Ohmi | 73/1.02 |
| 5,509,292 | 4/1996 | D'Appollonia | 73/1.06 |
| 5,518,015 | 5/1996 | Berget | 251/129.12 |
| 5,587,519 | 12/1996 | Ronge | 73/1.06 |
| 5,635,620 | 6/1997 | Ronge | 73/1.06 |
| 5,661,225 | 8/1997 | Ridgeway | 137/7 |

FOREIGN PATENT DOCUMENTS

| | | |
|---|---|---|
| 0 528 386A2 | 2/1993 | European Pat. Off. . |
| 0 664 449A1 | 7/1995 | European Pat. Off. . |

*Primary Examiner*—Denise L. Ferensic
*Assistant Examiner*—Ramyar Farid
*Attorney, Agent, or Firm*—Burns, Doane, Swecker & Mathis, L.L.P.

[57] ABSTRACT

A method of delivering a pure gas charged with a predetermined quantity of at least one gaseous impurity to an apparatus, comprising the steps of mixing at least two different auxiliary gases, including the impurity to form a mixture, diluting a sampled quantity of the mixture in the pure gas in a predetermined manner, delivering the pure gas charged with the impurity to the apparatus, wherein the auxiliary gases are stored in a reservoir in the form of a mixture of known composition, most of the auxiliary gases in the mixture having volume concentrations substantially of the same order of magnitude.

17 Claims, 4 Drawing Sheets

METHOD AND DEVICE FOR DELIVERING A PURE GAS CHARGED WITH A PREDETERMINED QUANTITY OF AT LEAST ONE GASEOUS IMPURITY TO AN APPARATUS

BACKGROUND OF THE INVENTION (i) Field of the Invention

The invention relates to a method and a device for delivering a pure gas charged with a predetermined quantity of at least one gaseous impurity to an apparatus, especially a trace-impurity analyzer such as an atmospheric-pressure ionization mass spectrometer.

(ii) Description of Related Art

In the field of the analysis of very-high purity gases, analyzers designed to detect impurities at very low concentrations (for example, from $10^{-2}$ to $10^{-5}$ ppm, or even from $10^{-3}$ to $10^{-6}$ ppm) are often used. Such an apparatus requires calibration at regular time intervals in order to ensure reliable and accurate operation.

Such a calibration is carried out by sequentially delivering to the analyzer firstly a pure or "zero" gas, that is to say a gas containing less than $10^{-5}$ ppm of impurities, and then a so-called "calibration" gas containing impurities in precisely known concentrations.

Such methods and such devices designed for the feed of an analyzer having a very high sensitivity are known from document FR-A-2714968 in the name of the Applicant and from document U.S. Pat. No. 5,239,856, also in the name of the Applicant.

The aforementioned FR document describes a device and a method in which a pure gas is charged with trace impurities using a battery of permeation cartridges connected in parallel to a unit for diluting the impurities in the pure gas. Each cartridge contains one gaseous impurity, such as $H_2O$, $CO_2$, CO, $O_2$, $CH_4$, $H_2$, etc., for example, which diffuses in very small quantity through a diaphragm for charging the pure gas flowing into the dilution unit.

This device has the drawback that each permeation cartridge creates, through its connection line to the dilution unit, a branch in which the flow stagnates, causing undesirable interactions with the walls of the line, such as, for example, absorption and desorption phenomena.

In addition, these connection branches are difficult to purge, compromising the use of such a battery of permeation cartridges with various kinds of pure gases.

Moreover, the flow rate of the impurity introduced through a permeation cartridge varies over time. Consequently, the accuracy with which the composition of the calibration gas is known decreases with time.

Another drawback of the device is connected with the operation of the permeation cartridges. A permeation cartridge is produced by a reservoir which includes an outlet closed off by a membrane, for example a silicone membrane, through which the impurity contained in the reservoir diffuses.

However, this membrane is not only permeable in the cartridge/dilution unit direction but also in the reverse, dilution unit/cartridge direction.

Thus, the pure gas in the connection branch can diffuse through the membrane into the cartridge, especially when the molecule is small, such as the molecule $H_2$. In the course of time, an unknown gas composition is created in the permeation cartridge, consequently compromising the precise generation of a calibration gas, especially in the case of the sequential use of the device with various kinds of pure gases.

Also currently, a procedure is carried out in the following manner: by using pure-gas/impurity I gas mixtures made up beforehand, the impurity I having a content which may be termed intermediate content, for example of the order of magnitude of 1 ppm.

Thus, for example, premixed bottles containing a few tens of ppm of CO or of hydrogen in nitrogen are used.

The required dilution steps are then performed, using the corresponding pure gas (Ar, $N_2$, He, etc.), of the gas in each premixture bottle, in order to end up with the final mixture containing the impurity I in the pure gas in question with a content, for example, of the order of magnitude of one ppb.

It may therefore be imagined that such a procedure is complex, expensive and causes multiplication of the sources of errors and contamination of the mixtures in the various manufacturing steps.

As regards document U.S. Pat. No. 5,239,856, this describes a method and a device for manufacturing a pure gas charged with trace impurities, according to which a certain quantity of gas is sampled from two gas sources, each gas of which constitutes an impurity in a pure gas.

The sampled gases are mixed and the mixture diluted in a dilution unit so as to obtain a very low concentration of the impurities in the pure gas, said concentration lying within a range extending from $10^{-5}$ ppm to $10^{-2}$ ppm, so as to deliver this calibration gas to a trace impurity analyzer which must be calibrated.

The accuracy with which the concentrations of the trace impurities in the pure gas are known depends not only on the quality of the dilution unit but also on the quality of manufacture of the gas mixture. However, in the case of the aforementioned US-A document, this accuracy depends on the uncertainty in the setting of the various mass flowmeters placed in the impurity sampling lines. By increasing the number of impurity sources and, consequently, the number of mass flowmeters for manufacturing the mixture, the accuracy with which the composition of the gas mixture is known decreases since the uncertainties in the flow rate of each mass flowmeter add together to form the uncertainty in the composition of the gas mixture obtained.

SUMMARY AND OBJECTS OF THE INVENTION

The present invention aims to alleviate these various drawbacks by providing a method and a device for delivering a pure gas charged with a predetermined quantity of at least one gaseous impurity to an apparatus, which is reliable, accurate and easy to employ.

For this purpose, the subject of the invention is a method of delivering a pure gas charged with a predetermined quantity of at least one gaseous impurity to an apparatus, according to which at least two different auxiliary gases, including said impurity, are mixed beforehand, a sampled quantity of said mixture is diluted in the pure gas in a predetermined manner and the pure gas charged with said impurity is delivered to the apparatus, being characterized in that said auxiliary gases are stored in a reservoir in the form of a mixture of known composition, the volume concentrations of most of the auxiliary gases in said mixture being substantially of the same order of magnitude, and the mixture in this reservoir is sampled in order to dilute it in the pure gas.

According to one of the embodiments of the invention, the mixture comprises at least one inert gas, the volume concentration of which is greater than the volume concentration of each of the other gases in the mixture.

The volume concentration of the inert gas is then advantageously greater than the sum of the volume concentrations of the other gases in the mixture.

According to an advantageous embodiment of the invention, the "order of magnitude" of the contents is one %.

Depending on the composition of the mixture (in particular depending on the desired calibration species), it will be noted that, for safety reasons, it is advantageous to use one or more inert gases in the mixture and to chose a gas concentration higher than the volume concentration of all the other constituents of the mixture. By virtue of such a mixture composition, oxidants, such as $O_2$ or CO, may coexist together with fuels, such as $CH_4$ for example, without there being a risk of the reservoir containing the mixture catching fire or exploding.

It is thus possible, by way of illustration, to adopt a content of about one % or a few % for the non-inert constituents of the mixture but to adopt a content of a few tens of % of the inert gas or gases in the mixture without thereby departing from the scope of the present invention, since the contents of all the components of the mixture are expressed as the same order of magnitude (%).

The subject of the invention is also a device for implementing the method defined hereinabove, comprising a source of pure gas, a source of said gaseous impurity and means of diluting the impurity in the pure gas in a predetermined manner, said means being connected to the apparatus via a gas delivery line, characterized in that said source of impurity comprises a reservoir containing said mixture of known composition of at least two different gases, including said impurity, the volume concentrations of most of the gases in said mixture being substantially of the same order of magnitude.

The device according to the invention may include one [lacuna] several of the following characteristics:

- the diluting means comprise means of splitting the flow from said source of pure gas, and several dilution stages placed in series, each stage comprising a first inlet line connected to an outlet line associated with said flow-splitting means and a second inlet line connected to a respective outlet line of the dilution stage placed just upstream, the second inlet line of the first dilution stage being connected to said reservoir via a line for sampling said mixture,
- the second inlet line of at least one dilution stage includes an additional flow-regulating element,
- each dilution stage comprises means of mixing the gases feeding the inlets of the stage, at least one dilution stage comprising an associated purge line which is connected via one end to said mixing means and in which is placed a diverter for controlling the pressure in the associated dilution stage,
- a dilution stage comprises a third inlet line connected to means for charging the pure gas with a predetermined quantity of $H_2O$,
- the means of splitting the flow from said source comprising [sic] a main line for delivering pure gas, said line being connected to several secondary output lines which are placed in parallel, each including a gaged restriction,
- the source of pure gas comprises a source of gas to be analyzed and a unit for purifying the gas output by the source,
- the purification unit comprises at least two purifiers, the inlet of each purifier being connected to a branching valve, which is placed in an inlet line of the purification unit, and the outlet of each purifier being connected to a valve for supplying the circuit with the purified gas, said valve being placed in a feed line of the diluting means,
- the inlet line of the purification unit and the feed line of the diluting means each emerge at one end in a corresponding purge line, an element for creating a pressure drop being placed in each corresponding purge line,
- each branching valve, as well as each circuit-supplying valve, comprises a first conduit permanently connected via a first end to an associated purifier, a second conduit, the second conduit of the branching valves being placed in the inlet line of the purification unit and those [sic] of the circuit-supplying valve being placed in the feed line of the diluting means, and an actuator which can be switched between a position for bringing the first conduit into communication with the second conduit and a position for isolating the first conduit from the second conduit, the second conduit being free of flow-stagnation volumes,
- the second conduit of each valve includes a chamber in which the second end of the first conduit emerges and each valve includes a closure element which is acted upon by the actuator of the valve, which closes off, in said isolating position, the end of the first conduit emerging in said chamber, and which is set back with respect to this end of the first conduit in said communication position,
- the end of the first conduit emerging in said chamber is provided with a seal projecting into the chamber and the closure element comprises an elastically deformable diaphragm forming part of the wall of the chamber opposite the seal, the diaphragm being pressed in a sealed manner onto the seal against the spring force of the diaphragm, in said isolating position, by a pusher of the actuator,
- each valve includes means for controlling the switching of the actuator between said communicating and isolating positions, the means for controlling each valve are connected to a control unit for isolating or bringing each valve into communication and the control unit includes logic means which prevent actuators associated with different purifiers from being simultaneously switched into the communicating position.

In addition, the subject of the invention is a reservoir containing a gas mixture of calibrated composition for charging a pure gas with impurities according to the method defined hereinabove and/or for constituting the source of impurities of the device defined hereinabove.

According to another characteristic, the reservoir contains at least two different gases having contents substantially of the same order of magnitude, and an inert gas in a greater proportion, preferably greater than the sum of the proportions of the other gases.

Furthermore, the subject of the invention is a valve for the device defined hereinabove.

Other characteristics and advantages of the invention will appear from the following description given by way of example but having no limiting character, with regard to the appended drawings in which:

DETAILED DESCRIPTION OF THE PREFERRED EMBODIMENTS

Figure 1:
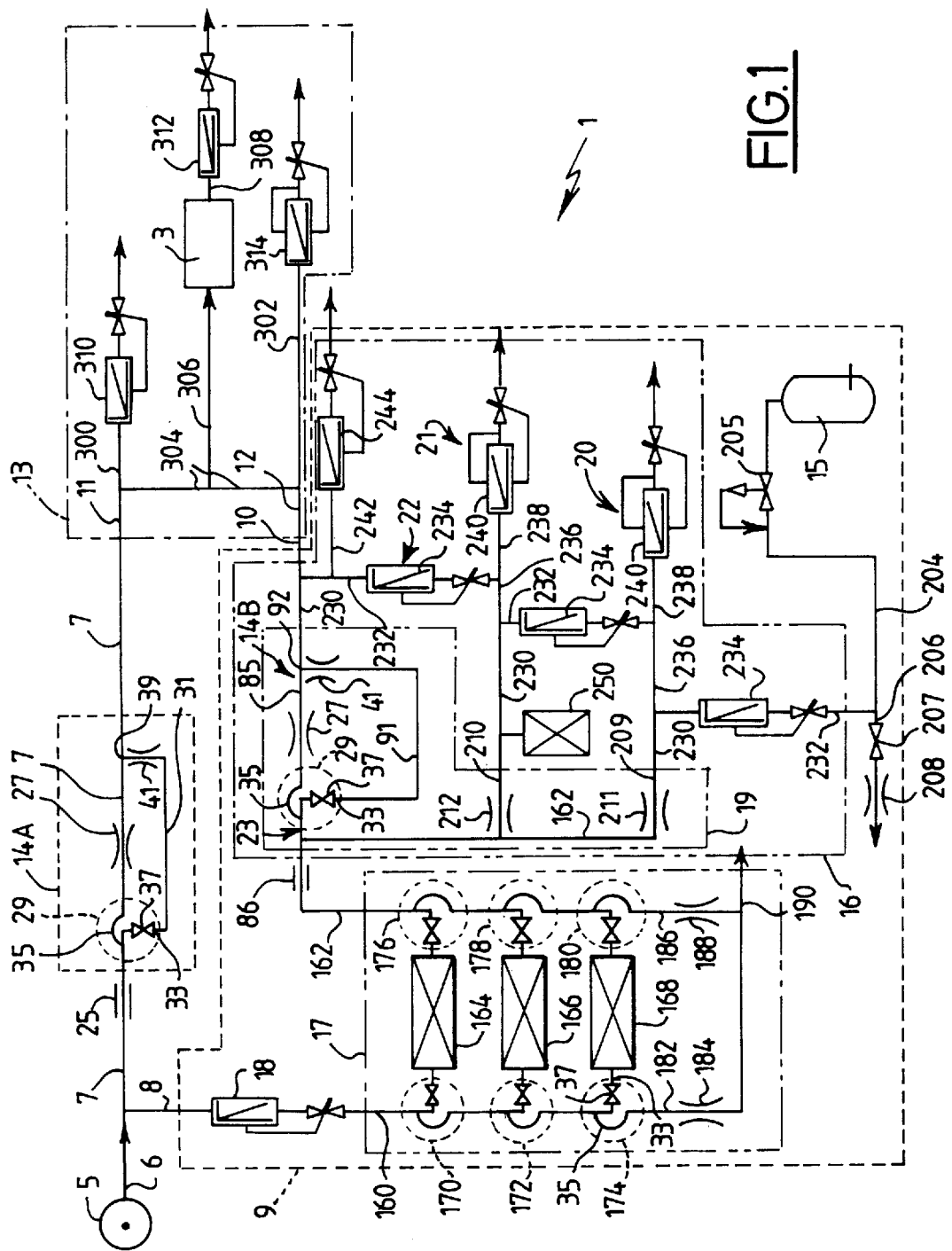
FIG. 1 is a general diagram of a plant for delivering, to an apparatus, either a gas to be analyzed or a pure gas, or else a gas charged with a predetermined quantity of impurities.

FIG. 1 shows a plant 1 for delivering gas to an apparatus 3 such as, for example, an apparatus for analyzing trace impurities in a gas, of the atmospheric-pressure ionization mass spectrometer. Such an analyzer 3 is capable of measuring trace impurities in a gas at very low concentrations of between $10^{-2}$ to [sic] $10^{-5}$ ppm, or indeed from $10^{-3}$ to $10^{-6}$ ppm. As will be explained in detail hereinbelow, this plant 1 delivers, to the apparatus 3, alternately a pure reference gas or "zero gas", that is to say a gas typically containing less than $10^{-4}$ ppm of impurities, a gas charged with a predetermined quantity of known gaseous impurities such as, for example, $H_2O$, $CO_2$, $CO$, $O_2$, $CH_4$, $H_2$, etc., at concentrations varying within a range extending from $10^{-5}$ ppm to $10^{-2}$ ppm, or else a gas to be analyzed. Furthermore, this plant must control the parameters relating to the introduction of the gas into the analyzer 3, such as the pressure and the flow rate.

In addition, this plant must allow the successive use of various kinds of gas to be analyzed.

For this purpose, a source 5 of a pressurized gas to be analyzed is connected via a sampling line 6 to the gas delivery plant 1. This source 5 comprises, for example, a single source of one kind of gas to be analyzed, or several pressurized sources of various kinds of gases, each connected via a sampling line to a device intended to deliver any one of the several gases to an apparatus, such as the device described in French Patent Application No. FR-960756096 filed in the name of the Applicant Company on Jun. 18, 1996.

The sampling line 6 is connected, on the one hand, to an analyzing line 7 and, on the other hand, to a feed line 8 of a device 9 for delivering a pure gas or a gas charged with a predetermined quantity of gaseous impurities.

The analyzing line 7 and an outlet line 10 of the delivery device 9 are each connected to a corresponding inlet line 11, 12 of a selection device 13 in order to deliver to the apparatus 3 either the gas contained in the analyzing line 7 or the gas output by the outlet line 10 of the delivery device 9.

A device 14A, for regulating a predetermined gas flow for gases to be analyzed that have substantially different molar masses, is placed in the analyzing line 7.

The delivery device 9 comprises a source of pure gas, a source 15 of impurities and means 16 of diluting the impurities in the pure gas in a predetermined manner.

The source of pure gas consists, on the one hand, of the source 5 of the gas to be analyzed and, on the other hand, of a unit 17 for purifying the gas output by the source 5, the flow of gas feeding the purification unit being controlled by means of a mass flow regulator 18 placed in the feed line 8.

The diluting means 16 include means 19 of splitting the gas flow output by the purification unit 17, which means feed several dilution stages 20, 21, 22 placed in series.

A branch 23 of the flow-splitting means 19 includes a device 14B for regulating a predetermined upstream gas pressure for gases having substantially different molar masses, the structure of this device 14B being identical to that of the regulating device 14A.

The structure and operation of the various units of the gas delivery plant 1 will be described in detail hereinbelow.

I. Device for regulating the flow of gases having substantially different molar masses.

I.1 Structure of the regulating device

The regulating device 14A is placed in the analyzing line 7. Placed upstream of this regulating device 14A is a pressure gauge 25 for determining the pressure upstream of the regulating device 14A.

The regulating device 14A includes, for the embodiment shown, a gaged restriction 27, for example a gaged orifice, placed in the analyzing line 7. Placed upstream of the orifice 27 is a branching valve 29, shown diagrammatically surrounded by dashes, for the selective use of a bypass line 31.

The valve 29 comprises a first conduit 33 permanently connected via one end to the bypass line 31. It furthermore comprises a second, always-open conduit 35 which is placed in the analyzing line 7.

The first conduit 33 and the second conduit 35 of the valve 29 may be brought into communication by an actuator 37, as will be explained in detail hereinbelow, which can switch between a position for bringing the first conduit 33 into communication with the second conduit 35 and a position for isolating the first conduit 33 from the second conduit 35. The bypass line 31 is connected via its other end 39, downstream of the orifice 27, to the analyzing line 7.

A second gaged orifice 41 is advantageously placed in the bypass line 31, as close as possible to the end 39 of the latter. Thus, a flow-stagnation volume, formed in the isolating position of the two conduits 33 and 35 by that part of the bypass line 31 lying between the orifice 41 and the end 39, is as small as possible.

The structure of the regulating device 14B is here identical to that of the device 14A. This is why the identical elements bear the same reference numbers.

This device thus includes a first orifice 27 placed in a feed line 85 for a pure gas output by the purification unit 17. Placed in this line 85 is a branching valve 29 identical to that of the device 14A. Connected to the conduit 33 of the valve 29 is one end of a bypass line 91. The other end of this line 91 is joined downstream of the orifice 27 to the feed line 85. A gaged orifice 41 is placed as close as possible to the end 92 via which the bypass line 91 is joined to the feed line 85.

I.2. Structure of the valve of the regulating devices:

An embodiment example of the valve 29 fitted in the regulating devices 14A and 14B is described in detail hereinbelow. Such a valve, of the electropolished DAD type, is for example derived from a valve marketed by the company NUPRO and manufactured by the company SWAGELOK.

Figure 3:
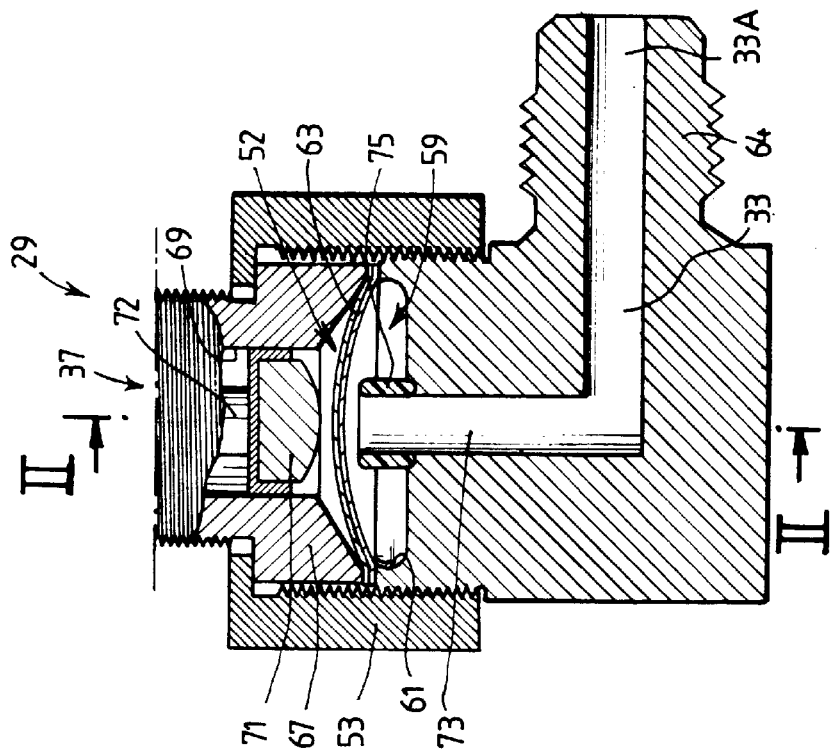
FIG. 3 is a sectional view, along the line III/III in FIG. 2, of the same valve in the communicating position.
Figure 2:
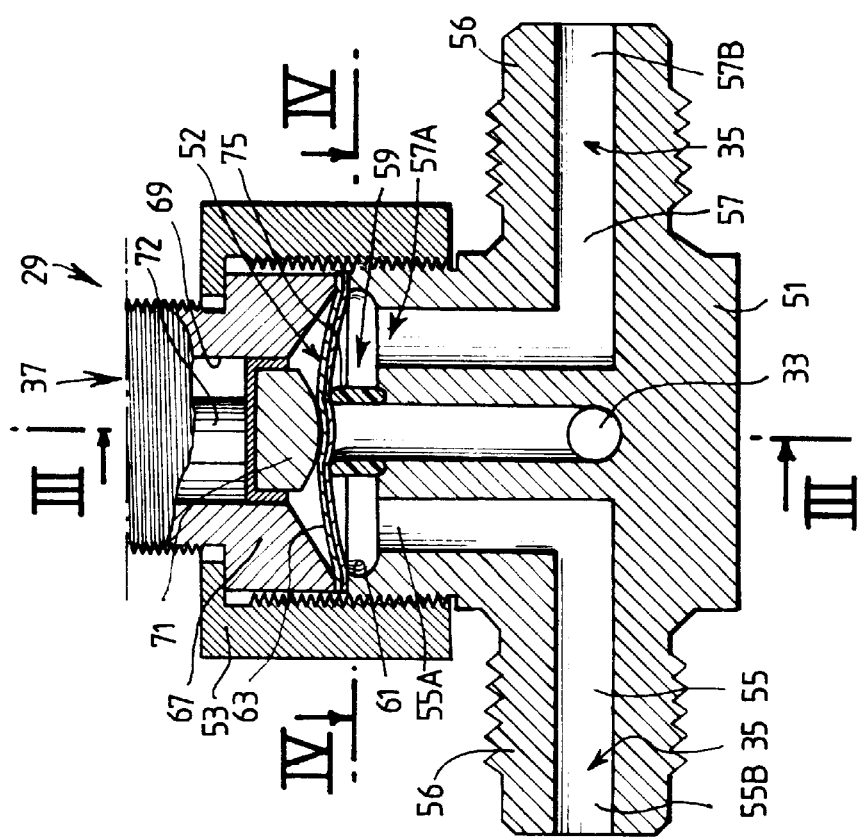
FIG. 2 is a sectional view along the line II/II in FIG. 3 of a valve of the regulating device in FIG. 1 as well as of a valve of a purification unit in FIG. 1, in the isolating position.

As shown in FIGS. 2 and 3, the valve 29 includes a body 51, in which the first conduit 33 and the second conduit 35 are made, a closure member 52 and an actuator 37, shown in part, which is screwed onto the body 51 by means of a nut 53.

The second conduit 35 (FIG. 2) is formed by two conduit sections 55 and 57 and by an axisymmetric annular chamber 59. Emerging in a lateral part of the bottom of this chamber 59 is one 55A, 57A of the two ends of each conduit section 55, 57.

The other end, 55B, 57B of each conduit section 55, 57 emerges in a respective lateral connector 56 on the body 51.

These ends 55B and 57B are diametrically opposed. The two connectors 56 are intended to be connected to the analyzing line 7, with regard to the regulating device 14A and to the feed line 85, with regard to the regulating device 14B.

The chamber 59 is formed by a substantially cylindrical recess 61, made in the upper face of the body 51, and by the closure member 52. This closure member itself consists of a combination of two diaphragms 63 joined together, these diaphragms covering the recess 61 and constituting the upper wall of the chamber 59.

The diaphragms 63 are made of an elastically deformable material, for example metal. Each diaphragm 63 is a disc, the central part of which is domed in a direction away from the body 51. The edge of the diaphragms 63 is clamped in a sealed manner between the annular edge of the recess 61 and an annular edge of a holding piece 67 which forms part of the actuator 37. The piece 67 is made in the form of a dish so as to allow movement of the domed part of the diaphragms 63.

In its central part, opposite the diaphragms 63, the holding piece 67 includes a guide bore 69 in which a pusher 71 driven by a rod 72 of the actuator 37 can slide.

The first conduit 33 of the valve 29 comprises a single straight blind hole, which extends perpendicularly to the axis defined by the ends 55B, 57B of the conduit sections 55, 57, and a connecting duct 73 which emerges at the center of the recess 61.

One end, 33A, of the first conduit 33 emerges in a respective lateral connector 64 on the body 51 and is intended to be connected to the bypass line 31 in the case of the device 14A or to the bypass line 91 in the case of the device 14B.

The end of the duct 73 emerging in the recess 61 includes a cylindrical seal 75 which is forcibly fitted into the body 51 of the valve and which projects into the chamber 59.

Figure 4A:
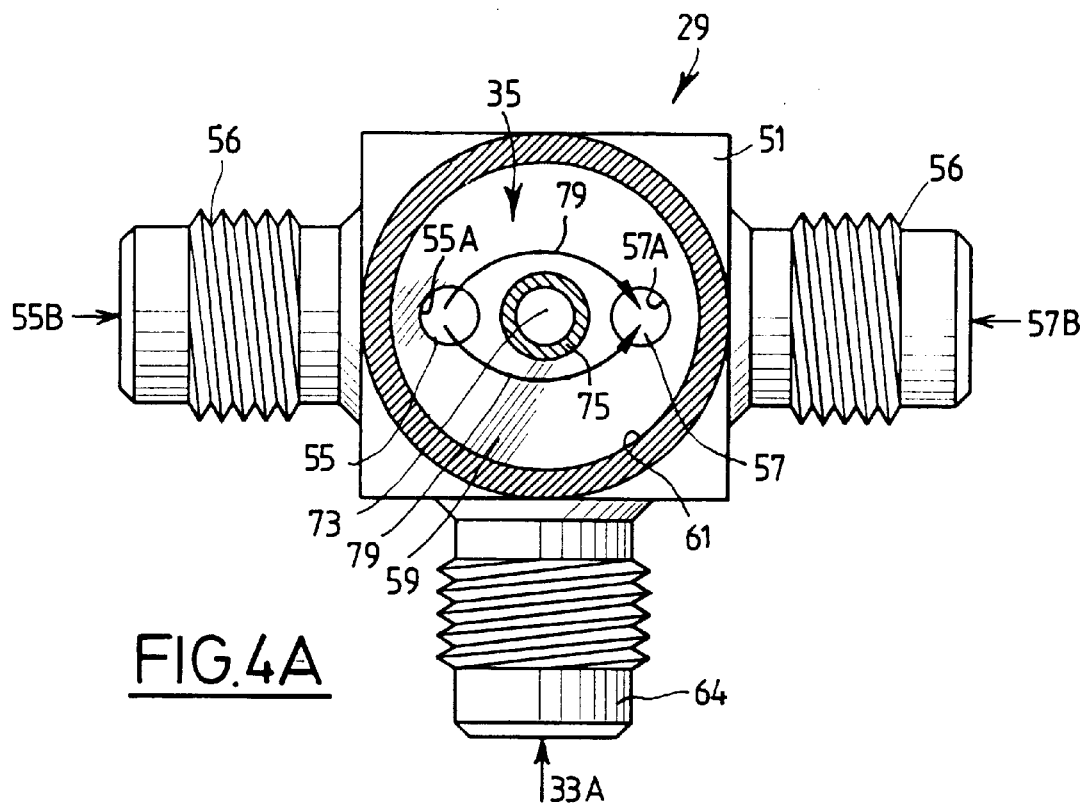
FIG. 4A is a sectional view, along the line IV/IV in FIG. 2, of the valve in the isolating position.

FIGS. 2 and 4A show the valve 29 in the position for isolating the first conduit 33 from the second conduit 35. In such a case, the central part of the diaphragms 63 is pressed in a sealed manner by the pusher 71 onto the seal 75 so that the duct 73 is isolated from the chamber 59.

Nevertheless, a gas introduced into the second conduit 35 of the valve flows freely, for example from the conduit section 55 into the chamber 59 and then into the conduit section 57, as shown by the arrows 79 in FIG. 4A. It is clear that the second conduit 35 of the valve thus formed has no flow-stagnation volume.

Figure 4B:
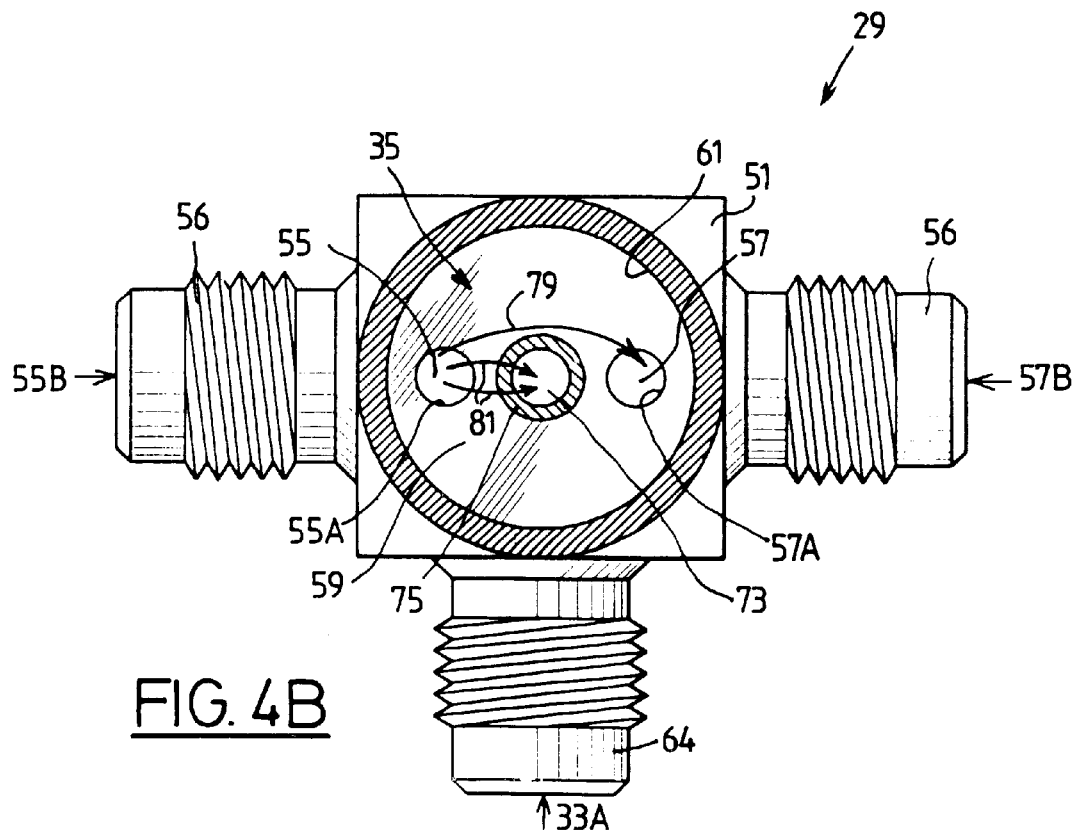
FIG. 4B is a sectional view, along the line IV/IV in FIG. 2, of the valve in the communicating position.

FIG. 3 and FIG. 4B correspond to a position for bringing the first conduit 33 into communication with the second conduit 35. In such a case, the pusher 71 is set back. The diaphragms 63 resume their initial domed shape by virtue of their spring force. Consequently, a free space is formed between the diaphragms 63 and the seal 75 so that the gas flowing in the second conduit 35 flows away largely via the duct 73 into the first conduit 33, as shown by the arrows 81 in FIG. 4B.

I.3. Operation of the regulating device:

The operation of the regulating devices 14A, 14B are explained hereinbelow with regard to FIG. 1. For this purpose, two operating methods will be distinguished.

In a first operating mode, the pressure upstream of the regulating device is imposed and the flow rate must be approximately the same for two gases having substantially different molar masses. This operating mode corresponds to the device 14A placed in the analyzing line 7.

In a second operating mode, the gas flow rate upstream of the regulating device is imposed and it is desired to establish a sonic flow regime. This operating mode corresponds to that produced by the regulating device 14B.

I.3.1. Imposed pressure operation:

For a light gas, such as hydrogen for example, the valve 29 of the regulating device 14A is switched into the position for isolating the first conduit 33 from the second conduit 35. The gas from the source 5 flows freely in the analyzing line 7 through the second conduit 35 and the orifice 27. In the case of a flow in sonic regime, that is to say in the case in which the ratio between the pressure upstream of the orifice 27 and the pressure downstream of this orifice is greater than 2, it is known that the volume flow rate $D_{27}$ of the gas through the orifice 27 is equal to:

$$D_{27} = K \times P \times S_{27} \times M^{-1/2}$$

where:
P=pressure upstream of the orifice 27,
$S_{27}$=cross section of the orifice 27,
M=molar mass of the gas flowing through the orifice, and
K=constant which depends on the temperature and nature of the gases.

By virtue of the fact that the conduit 35 of the valve 29 has no flow-stagnation volume and that the orifice 41 of the bypass line 31 is placed close to the end 39 of this line, the regulating device 14A introduces only a negligible flow-stagnation volume into the analyzing line 7 in the position for isolating the first conduit 33 from the second conduit 35 of the valve.

In the case of a gas having a greater molar mass, such as $N_2$ for example, for the same pressure the flow rate through the orifice 27 falls proportionally to the square root of the ratio of the molar masses of the two gases, for example in the case of $N_2$ and $H_2$, to approximately one quarter of the flow rate obtained in the case of $H_2$. In this case, in order to maintain the flow rate delivered by the analyzing line 7 at approximately the same level as the flow rate of a gas of low molar mass, the valve 29 is switched to the state for bringing the first conduit 33 into communication with the second conduit 35. The gas then flows not only through the orifice 27 but also into the bypass line 31 through the orifice 41.

To the flow rate $D_{27}$ is then added, at the connection of the analyzing line 7 and the bypass line 31, the flow rate $D_{41}$ which is given, in sonic regime, by the equation:

$$D_{41} = K \times P \times S_{41} \times M^{-1/2}$$

The nomenclature used is analogous to that used for the flow rate $D_{27}$.

In order for the flow rate controlled by the regulating device 14A to be approximately equal in the case of two gases having respectively a molar mass $M_1$ and $M_2$, the cross section $S_{41}$ of the orifice 41 is chosen in such a way that it satisfies the equation:

$$S_{41} = ((M_1^{1/2}/M_2^{1/2}) \times S_{27}) - S_{27}$$

where $M_1$ is the molar mass of a gas having a high molar mass, and $M_2$ is the molar mass of a gas having a low molar mass.

Preferably, the cross section $S_{41}$ of the orifice 41 is chosen in such a way that the flow rate of $H_2$ in the isolating state of the valve 29 is comparable to the flow rate of $N_2$ through the orifice 27 and the orifice 41 in the communicating state of the valve 29.

I.3.2. Imposed-flow-rate operation:

This operating mode of the regulating device is beneficial in the case in which the flow rate upstream of the regulating device is imposed and in which it is necessary to establish a sonic regime for flow-regulating orifices, such as, for example, those of the flow-splitting means 19. The gas flow rate upstream of the regulating device 14B is imposed by the flow regulator 18.

It will be understood here that the "sonic" regime is preferred and that the fact of departing too far therefrom quite simply makes it difficult to calculate the flow distribution. It is therefore a question of finding a ratio of the upstream and downstream flow rates lying between 1.5 and 30.

In order to explain the imposed-flow-rate operation, it will be assumed that only the regulating device 14B alone placed [sic] in the feed line 85, as was described with regard to the device 14A. In the case in which the device 14B is placed in the flow-splitting means 19, the reasoning presented above applies correspondingly.

With a volume flow rate imposed, the pressure upstream of the orifice 27 in the isolating position of the valve 29 is given by the equation:

$$P = K' \times D_{18} \times M^{1/2} \times S_{83}^{-1}$$

with:

$D_{18}$=volume flow rate imposed by the flow regulator 18, $K'$=a constant which depends on the nature of the gas and on the temperature, $S_{27}$=the cross section of the orifice 27.

The cross section of the orifice 27 is dimensioned in such a way that, for a light gas such as $H_2$, sonic conditions are attained upstream of the orifice 27.

In the case of a gas, such as $N_2$, having a high molar mass, the pressure upstream of the orifice 27, for the same flow rate, is approximately four times greater compared to the upstream pressure obtained in the case of $H_2$.

This is why the valve 29 is switched to the state for bringing the first conduit 33 into communication with the second conduit 35. The gas then flows not only through the orifice 27 but also through the orifice 41. The pressure upstream of the orifice 27 and of the orifice 41 is given by the equation $$P = K' \times D_{18} \times M^{1/2} \times (S_{27} + S_{41})^{-1}$$

with:

$S_{41}$=cross section of the orifice 41.

In order for the pressure upstream of the regulating device 14B to attain sonic conditions for two gases of different molar mass, the cross section $S_{41}$ of the orifice 41 is chosen in such a way that it satisfies the equation $$S_{41} = ((M_1^{1/2}/M_2^{1/2}) \times S_{27}) - S_{27}$$

where $M_1$ is the molar mass of a gas of high molar mass and $M_2$ is the molar mass of a gas having a low molar mass.

Of course, instead of the orifices 27 and 41 it is possible to use any gaged restrictions, such as, for example, capillaries, or frits.

Moreover, provision may be made to use diaphragm valves 29 which include means for driving the actuator 37 between the communicating and isolating positions, such as pneumatic valves or electromagnetically-operated valves. The means for controlling the movement of the actuator of the valve are then connected to a control unit, such as a microcomputer or a controller, for example.

II. Device for delivering a pure gas charged with a predetermined quantity of gaseous impurities The various units of the device 9 for delivering a pure gas charged with a predetermined quantity of gaseous impurities, namely the purification unit 17, the source of impurities 15 and the means 16 of diluting the impurities in the pure gas in a predetermined manner, are presented in detail hereinbelow.

II.1. Purification unit:

II.1.1. Structure of the purification unit

The purification unit 17 comprises an inlet line 160 and a line 162 for delivering a pure gas, between which are placed in parallel three purifiers 164, 166, 168, such as a nitrogen purifier, a hydrogen purifier and an argon/helium purifier, for example.

The inlet of each purifier is joined via a branching valve 170, 172, 174 to the inlet line 160. The outlet of each purifier 164, 166, 168 is connected to the delivery line 162 of the purification unit 17 by means of a valve 176, 178, 180 for supplying the circuit with the purified gas.

The valves 170 to 180 are identical to the valves 29 of the regulating devices 14A, 14B.

Thus, each branching valve 170, 172, 174, as well as each valve 176, 178, 180 for supplying the circuit with the purified gas, comprises a first conduit 33 permanently connected at one end to a corresponding purifier 164, 166, 168. The second conduits 35 of the branching valves 170, 172, 174 are placed in the inlet line 160. The second conduits 35 of the valves 176, 178, 180 for supplying the circuit with the pure gas are placed in the delivery line 162.

The feed line 160 is connected, downstream of the valve 174, to a purge line 182 in which an element 184 for creating a pressure drop, such as a gaged orifice, is placed.

The outlet line 162 is connected, at the end opposite the diluting means 16, to an associated purge line 186 in which an element for creating a pressure drop 188, such as a gaged orifice, is placed.

The purge lines 182 and 186 come together into a common purge line 190 downstream of the gaged orifices 184 and 188.

II.1.2. Operation of the purification unit

Depending on the kind of gas which is output by the source 5, the inlet valve 170 of the purifier 164 associated with this gas and the valve 176 of the corresponding outlet are, for example, switched to the state for bringing the conduits 33 and 35 into communication with each other. The gas to be analyzed from the source 5 flows freely through the purifier 164, which purifies this gas. The other valves 172, 174, 178 and 180 are in the isolating state.

If the nature of the gas output by the pressure source 5 is changed, the valves 170, 176, which hitherto were open, are switched to the isolating state and the valves associated with another purifier are switched to the communicating state.

By virtue of the construction of the valves 170 to 180 and by virtue of the orifices allowing a leakage flow, the feed line 160 and the outlet line 162 are continuously purged. This purification unit 23 furthermore has the advantage that it can be used with various kinds of gases to be purified and that it is virtually free of flow-stagnation volumes.

Advantageously, in order to switch the valves, diaphragm valves are used which include means for controlling the switching of the actuator between the communicating and isolating positions, such as pneumatic or electromagnetically-operated valves for example. The means for controlling the movement of the actuator of each valve are connected to a control unit, such as a microcomputer or a logic controller for example. This control unit includes switching logic means. These logic means are produced, for example, by a computer program charged into the microcomputer which excludes the possibility of two purifiers being simultaneously in communication with the feed line 160 and the outlet line 162.

II.2. The source of impurities

The source of impurities 15 comprises a reservoir containing a mixture of various kinds of gases such as, for example, $N_2$, $CO_2$, CO, $O_2$, $CH_4$, $H_2$, Ar, Kr, Xe, He, etc. This mixture has been produced in such a way that the volume concentrations of most of the gases in this mixture are of the same order of magnitude [sic] (here, one %).

For safety reasons, the concentration of an inert gas, such as helium for example, is chosen to be much higher than the volume concentration of all the other constituents of the mixture. By virtue of such a composition of the mixture, oxidants, such as $O_2$ or CO, may coexist together with fuels, such as $CH_4$, for example, without their being a risk of the reservoir 15 catching fire or exploding.

In order to know accurately, after dilution, the contents of the trace impurities in the pure gas, the composition of the mixture in the reservoir 15 has been accurately determined beforehand using gas analysis means, such as a gas chromatograph for example. The reservoir 15 may, for example, be a bottle under a high pressure (typically 200 bar).

The gases in the mixture are sampled or introduced into the diluting means 16 via a sampling line 204 into which a downstream pressure regulator 205 is placed. The sampling line 204 emerges in an associated purge line 206 in which a shutoff valve 207 and an element for creating a pressure drop, such as a gaged orifice 208, are placed.

II.3. The means of diluting the gaseous impurity in the pure gas in a predetermined manner The diluting means 16 comprise, on the one hand, the means 19 of splitting the flow of pure gas delivered by the feed line 162 at the outlet of the purification unit 17 and, on the other hand, three dilution stages 20, 21, 22 placed in series. A pressure gage 86 is placed in the line 162 upstream of the splitting means.

The splitting means 19 comprise the regulating device 14B and two lines 209, 210, said regulating device and said lines being connected in parallel with the feed line 162. A gaged restriction 211, 212, such as a gaged orifice, is placed in each line 209, 210.

The line from the regulating device 14B as well as the lines 209 and 210 with their respective orifices 211, 212 each form a branch for feeding a corresponding dilution stage 20, 21, 22, with pure gas.

The operation of such flow-splitting means is described in detail in Patent Application FR-A-2714968 in the name of the Applicant Company. This is why this operation will not be described hereinbelow.

Figure 5:
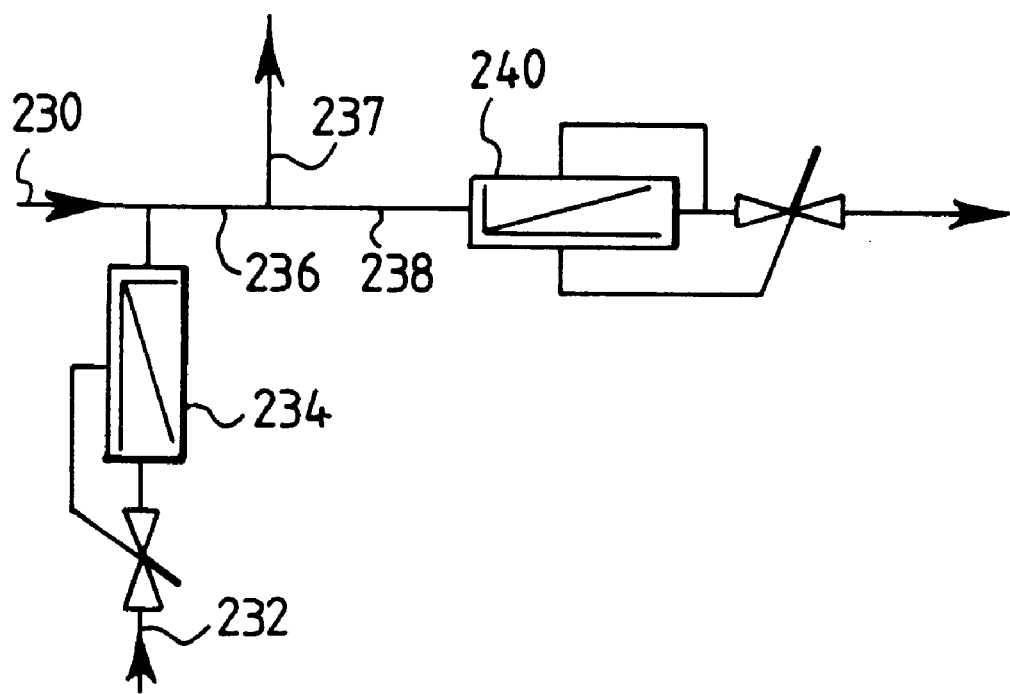
FIG. 5 is a diagram of a dilution stage.

FIG. 5 shows an example of a dilution stage 20, 21 or 22. A dilution stage 20, 21 or 22 comprises a pure gas feed line 230, connected to a corresponding branch of the splitting means 19, and an impurity-containing gas feed line 232.

A mass flow regulator 234 is placed in the feed line 232 so as to enable the degree of dilution of the dilution stage to be varied.

The feed lines 230 and 232 are joined together in such a way that they emerge in a common mixing line 236. The line 236 emerges, on the one hand, in an outlet 237 of the dilution stage. This outlet line 237 is connected to the feed line 232 of the dilution stage placed just downstream.

On the other hand, in the case of the dilution stages 20 and 21, the dilution line 236 is connected to a purge line 238 in which a diverter 240 is placed. The pressure of a diverter in one dilution stage is set in such a way that, on the one hand, the sonic conditions for the diluting means are preferably satisfied and, on the other hand, the pressure set is slightly higher than the pressure set in the diverter placed in a dilution stage downstream, so as to ensure that the gases flow toward the analyzer 3.

The feed line 232 of the dilution stage 20 is joined, downstream of the pressure regulator 205 and upstream of the shutoff valve 207, to the sampling line 204.

The outlet line 237 of the final dilution stage 22 emerges in the outlet line 10 of the delivery device 9, downstream of the regulating device 14B.

The flows at the inlet of each dilution stage are set in such a way that a dilution, for example, of approximately $1/1000$ of the gas output by the line 232 in the pure gas output by the line 230 is obtained.

Of course, the "zero" impurity quantity is also a predetermined quantity of trace impurities which the device has to deliver to the analyzer 3. This is why the feed line 232 of the final dilution stage 22 includes a bypass line 242 in which a mass flow regulator 244 is placed.

The outlet line 10 of the delivery device 9 outputs a pure gas in the case in which the regulator 244 is set to a flow rate greater than that of the regulator 234 of the dilution stage 22 and it outputs a pure gas charged with a predetermined quantity of trace impurities in the case in which the flow rate controlled by the regulator 244 is less than that of the regulator 234.

The impurity $H_2O$ is generated here by a permeation cartridge 250 outputting approximately 250 ng/min and connected as a branch off the pure gas line 230 of the second dilution stage 21.

This permeation cartridge contains water heated to 50° C. and includes, at one end, a silicone membrane through which the $H_2O$ molecule diffuses.

It will be noted that the cartridge could be placed on the first stage for a higher permeation rate, the permeation rate being chosen to generate in the line a content equivalent to that of the gaseous impurities present at this level of dilution.

Table 1 below shows, for a predetermined composition of the gas mixture in the reservoir 15, two examples of manufacture of a pure gas charged with a predetermined quantity of trace impurities which is output by the outlet line 10 of the delivery device 9, these examples being made in one case with hydrogen as the pure gas and in one case with nitrogen as the pure gas.

It will therefore be imagined that the reserve 15 represents a single bottle containing all the impurities required for the calibration of the apparatus (instead of many Impurity I/Pure gas mixtures), the initial order of magnitude of the content of most of the constituents of the mixture being particularly easy to establish, whilst still allowing calibrated impurities with extremely low contents (ppm, ppb or even lower) to be obtained at the inlet.

TABLE 1

| Impurities | Composition of the reservoir in vol. % | Concentration of the impurities, $H_2$ pure gas | Concentration of the impurities, $N_2$ pure gas |
|---|---|---|---|
| $O_2$ | 5% | 0.20 ppb | 1.62 ppb |
| $H_2$ | 5% | — | 1.62 ppb |
| $N_2$ | 5% | 0.20 ppb | 1.62 ppb |
| Ar | 5% | 0.20 ppb | 1.62 ppb |
| CO | 5% | 0.20 ppb | 1.62 ppb |
| $CO_2$ | 5% | 0.20 ppb | 1.62 ppb |

TABLE 1-continued

| Impurities | Composition of the reservoir in vol. % | Concentration of the impurities, $H_2$ pure gas | Concentration of the impurities, $N_2$ pure gas |
|---|---|---|---|
| $CH_4$ | 5% | 0.20 ppb | 1.62 ppb |
| Xe | 5% | 0.20 ppb | 1.62 ppb |
| Kr | 5% | 0.20 ppb | 1.62 ppb |
| He | 55% | 2.19 ppb | 17.85 ppb |
| $H_2O$ | permeation cartridge | 0.81 ppb | 1.58 ppb |

By virtue of the fact that the initial composition of the reservoir 15 has been accurately determined beforehand and that these impurities are diluted in a very precise manner, a pure gas containing a precisely known concentration of trace impurities is obtained.

In addition, using the flowmeters 234 in the feed line 232 of each dilution stage 20, 21, 22, it is possible to vary the range of concentrations of the trace impurities by a factor of 100.

By virtue of the fact that the reservoir 15 contains a mixture of several gases, this constitutes trace impurities in various pure gases. Together with the purification unit 17, the generation of a pure gas charged with predetermined quantities of given trace impurities is therefore considerably facilitated by this device.

III. Device for selecting one of the two gases:

As has already been described, the device 13 for selecting one of the two gases comprises two feed lines 11, 12, one of which, 11, is connected to the analyzing line 7 and the other, 12, to the outlet line 10 of the delivery device 9.

Each feed line 11, 12 emerges in a respective purge line 300 and 302. The feed lines 11 and 12 are connected together by means of a connecting line 304. The connecting line 304 is connected to the analyzer 3 via a gas delivery line 306. The outlet of the analyzer 3 also emerges in an associated purge line 308. The purge lines 300 and 308 each include a mass flow regulator 310, 312. A diverter 314 is placed in the purge line 302.

In order to deliver the gas contained in the line 11 to the analyzer 3, the sum of the flow rates $D_{310}+D_{312}$ controlled by the flow regulators 310 and 312 is set to a flow rate which is less than the flow rate $D_{11}$ of the flow output by the line 11. In order to deliver a calibration gas, that is to say either a pure gas or a gas charged with a predetermined quantity of impurities, to the analyzer 3, the flow rate $D_{310}$ of the flow regulator 310 is set so that it is greater than the flow rate $D_{11}$ of the flow coming from the line 11, and the flow rate $D_{312}$ controlled by the flow regulator 312 is set so that it is slightly less than the gas flow rate $D_{12}$ in the line 12. The pressure of the gas introduced into the analyzer 3 is controlled by the diverter 314 placed in the purge line 302.

Advantageously, by means of such an arrangement, it is possible not only to select, for delivery to the analyzer 3, the gas to be analyzed or the calibration gas, but it is also possible to control parameters relating to the introduction of the gases into the analyzer 3, such as the flow rate and the pressure.

By virtue of the fact that a smaller number of regulating components are used compared with the device described in the aforementioned French Patent Application, the cost of the plant is considerably reduced. In addition, a reduction in the number of regulating components also means that there is an increase in the accuracy and reliability of the apparatus 3.

We claim:

1. A method of delivering a pure gas charged with a predetermined quantity of at least one gaseous impurity to an apparatus, comprising the steps of:

mixing at least two different auxiliary gases, at least one of said auxiliary gases being said impurity, to form a mixture, storing said auxiliary gases in the form of said mixture in a reservoir, the reservoir containing solely said mixture, diluting a sampled quantity of said mixture in the pure gas in a predetermined manner, delivering the pure gas charged with said impurity to the apparatus, wherein the auxiliary gases in said mixture have volume concentrations substantially of the same order of magnitude and all of the auxiliary gases have volume concentrations within two orders of magnitude of any other ones of the auxiliary gases.

2. The method according to claim 1 wherein the mixture comprises at least one inert gas having a volume concentration greater than the volume concentration of each of the other gases in the mixture.

3. The method according to claim 2 wherein the volume concentration of the inert gas is greater than the sum of the volume concentrations of the other gases in the mixture.

4. The method according to claim 1, wherein said order of magnitude is 1%.

5. A device for delivering a pure gas charged with a predetermined quantity of at least one gaseous impurity to an apparatus, comprising a source of pure gas, a source of gaseous impurity and means of diluting the impurity in the pure gas in a predetermined manner, said means being connected to the apparatus via a gas delivery line, wherein said source of impurity comprises a reservoir containing solely a mixture of at least two different gases, at least one of said at least two different gases being said impurity, the gases in said mixture having volume concentrations substantially of the same order of magnitude and all of the gases have volume concentrations within two orders of magnitude of any other ones of the gases.

6. The device according to claim 5 wherein the diluting means comprise means of splitting flow from said source of pure gas, and several dilution stages placed in series, each stage comprising a first inlet line connected to an outlet line associated with said flow-splitting means and a second inlet line connected to a respective outlet line of the dilution stage placed just upstream, wherein the second inlet line of the first dilution stage is connected to said reservoir via a line for sampling said mixture.

7. The device according to claim 6, wherein the second inlet line of at least one dilution stage includes an additional flow-regulating element.

8. The device according to claim 6, in which each dilution stage further comprises means of mixing the gases feeding the inlets of the stage, wherein at least one dilution stage comprises an associated purge line which is connected via one end to said mixing means and in which is placed a diverter for controlling the pressure in the associated dilution stage.

9. The device according to claim 6, wherein a dilution stage comprises a third inlet line connected to means for charging the pure gas with a predetermined quantity of $H_2O$.

10. The device according to claim 6, wherein the means of splitting the flow from said source comprise a main line for delivering pure gas, said line being connected to several secondary output lines which are placed in parallel, each including a gaged restriction.

11. The device according to claim 5, wherein the source of pure gas comprises a source of gas to be analyzed and a purification unit for purifying gas output by the source.

12. The device according to claim 11, wherein the purification unit comprises at least two purifiers, each of which has an inlet and an outlet, the inlet of each purifier being connected to a branching valve, which is placed in an inlet line of the purification unit, and the outlet of each purifier being connected to a circuit-supplying valve for supplying the purified gas, said valve being placed in a feed line of the diluting means.

13. The device according to claim 12, wherein the inlet line of the purification unit and the feed line of the diluting means each emerge at one end in a corresponding purge line, an element for creating a pressure drop being placed in each corresponding purge line.

14. The device according to claim 12, wherein each branching valve, as well as each circuit-supplying valve, comprises a first conduit including first and second ends which is permanently connected via the first end to an associated purifier, a second conduit, the second conduit of the branching valves being placed in the inlet line of the purification unit and that of the circuit-supplying valves being placed in the feed line of the diluting means, and an actuator which can be switched between a position for bringing the first conduit into communication with the second conduit and a position for isolating the first conduit from the second conduit, the second conduit being free of flow-stagnation volumes.

15. The device according to claim 14 wherein the second conduit of each valve includes a chamber having a wall in which the second end of the first conduit emerges and each valve includes a closure element which is acted upon by the actuator of the valve, which closes off, in said isolating position, the end of the first conduit emerging in said chamber, and which is set back with respect to this end of the first conduit in said communication position.

16. The device according to claim 15, wherein the end of the first conduit emerging in said chamber is provided with a seal projecting into the chamber and the closure element comprises an elastically deformable diaphragm having a spring force and forming part of the wall of the chamber opposite the seal, the diaphragm being pressed in a sealed manner onto the seal against the spring force of the diaphragm, in said isolating position, by a pusher of the actuator.

17. The device according to claim 14, wherein each valve includes means for controlling the switching of the actuator between said communicating and isolating positions, and the means for controlling each valve are connected to a control unit for isolating or bringing each valve into communication and the control unit includes logic means which prevent actuators associated with different purifiers from being simultaneously switched into the communicating position.

* * * * *